US00PP31475P3

(12) United States Plant Patent
Wang

(10) Patent No.: US PP31,475 P3
(45) Date of Patent: Feb. 25, 2020

(54) CHINESE REDBUD PLANT NAMED 'CHONGYANG'

(50) Latin Name: *Cercis chinensis*
Varietal Denomination: Chongyang

(71) Applicant: HENAN MINGPIN COLORIZED SEEDLING CO., LTD, Suiping, Henan (CN)

(72) Inventor: Huaming Wang, Henan (CN)

(73) Assignee: HENAN MINGPIN COLORIZED SEEDLING CO., LTD, Suiping County, Henan Province (CN)

( * ) Notice: Subject to any disclaimer, the term of this patent is extended or adjusted under 35 U.S.C. 154(b) by 81 days.

(21) Appl. No.: 15/731,042

(22) Filed: Apr. 11, 2017

(65) Prior Publication Data

US 2017/0311503 P1 Oct. 26, 2017

(51) Int. Cl.
*A01H 5/02* (2018.01)
*A01H 6/00* (2018.01)

(52) U.S. Cl.
USPC ..... Plt./216
CPC ..... *A01H 5/02* (2013.01); *A01H 6/00* (2018.05)

(58) Field of Classification Search
USPC ..... Plt./216
CPC ..... A01H 5/02
See application file for complete search history.

(56) References Cited

U.S. PATENT DOCUMENTS

PP29,290 P2 * 5/2018 Westervelt ..... A01H 5/02 Plt./216

* cited by examiner

*Primary Examiner* — Kent L Bell

(57) ABSTRACT

'Chongyang' is a distinctive variety of Chinese redbud plant, which is characterized by its florescence.

14 Drawing Sheets

Genus and species: *Cercis chinensis*.
Variety denomination: 'Chongyang'.

BACKGROUND OF THE INVENTION

The present invention relates to a new and distinct variety of Chinese redbud plant, which is given the varietal denomination of 'Chongyang'.

In September 2005, a naturally occurring whole plant mutation Chinese redbud plant was found among seedlings in Yushan Village, Suiping County, Henan Province, China. The mutated plants bloomed out in both spring as ordinary Chinese redbud plant, and late September. Autumn flowers had a same color as spring flowers, and also had a huge amount. However, autumn florescence was longer than spring florescence. The autumn flowers withered after frost.

In April 2006, branches of the mutated Chinese redbud plant were grafted to a normal Chinese redbud plant through whip grafting. In late September 2006, the grafted plant bloomed again and grew well.

In spring 2007, the grafted plant was asexually reproduced by laying and grafting. Characteristics thereof were all kept.

From 2008-2013, after generations of asexual reproduction, no atavism or further mutation was observed. All generations grew well. Characteristics of the distinct variety were kept stable.

The seedlings base mentioned above has *Cercis chinensis* and *Cercis canadensis* 'Forest Pansy'. The soil is excellent with sufficient drainage. There is no pollution source around, and the nursery is closed with only one entrance. The local summer average maximum temperature is 38 degrees Celsius, the average winter minimum temperature is −6 degrees Celsius. Annual average rainfall is 800 mm.

The new and distinct variety of Chinese redbud plant is not commercially available.

SUMMARY OF THE NEW VARIETY

'Chongyang' is a distinct variety of Chinese redbud plant, belonging to deciduous-leaved shrubs and small trees. A whole plant is 2-4 m high and planted at about 150 meters above sea level. Twigs are coated or glabrous. Leaves are heart-shaped and green (RHS GREEN 140B to 140A or 143C to 143A) (according to Royal Horticultural Society Colour Chart Sixth Revised Edition (2015), same below), which are smooth and glabrous on top surfaces, and slightly rough and glabrous or slightly coated on bottom surfaces. The leaves are 5-8 cm long and 5-6 cm wide. Flowers are densely clustered, butterfly-shaped and rose-red (RHS RED-PURPLE N57D to N57B or 58D to 58A) with short pedicels. The petioles are 1.8 cm-4.2 cm long. There are two florescences in a year. A first florescence is from March to April in spring, wherein flowers appear before leaves. A second florescence is from September to November in autumn, wherein the leaves and the flowers exist at the same time. In autumn, a few flowers bloom out in advance, and then all flowers gradually bloom out. Autumn flowers have a same color as spring flowers, and also have a huge amount. However, the autumn florescence is longer than the spring florescence. The autumn flowers wither after frost. Buds are 0.4 cm-0.6 cm long and 0.2 cm-0.3 cm wide, which are rose red (RHS RED-PURPLE 58A). Inflorescence is clustered. Petals are purplish red (RHS RED-PURPLE N57D to N57B or 58D to 58 A). Sepals are rose red (RHS RED-PURPLE 58B). Peduncles are 0.5 cm-1 cm long. There are one pistil and nine stamens for each flower. Fruits are flat pods which is green (RHS GREEN 141D-A or YELLOW-GREEN N144D-A), wherein a length thereof is 3-8 cm and a width is 1-2.5 cm. A few fruits are produced in spring while no fruit is produced in autumn. Trunks have irregular and longitudinal cracks, and are dark gray (RHS GREY GROUP 201D to 201A). Stems are also dark gray (RHS GREY GROUP 201D to A).

DETAILED DESCRIPTION

The accompanying colored photographs illustrate the overall appearance of the new and distinct variety of 'Chongyang'. The descriptions disclosed herein are based upon observations of the plant growth.

Figure 1:
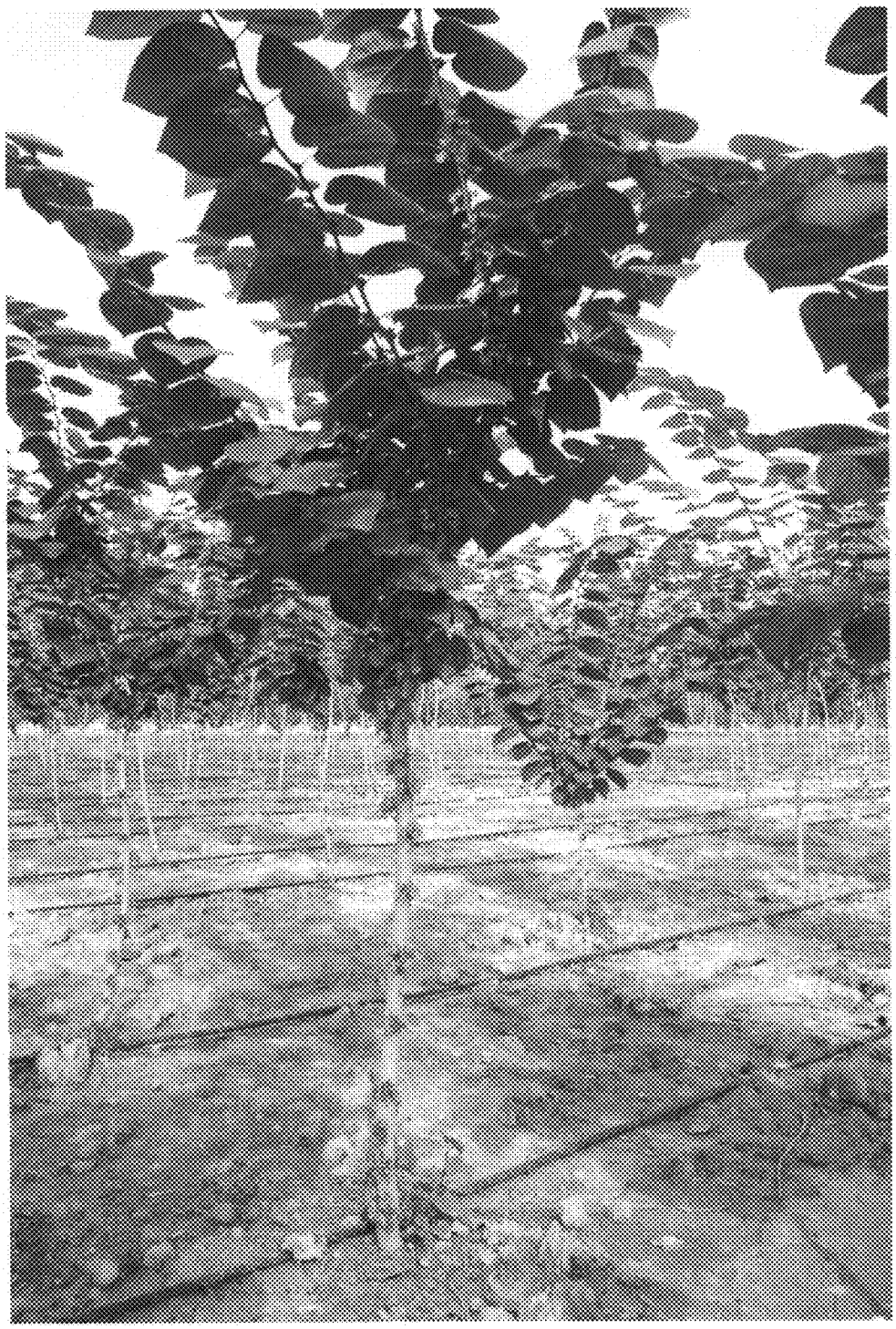
FIG. 1 is a color photograph of the new invention, 'Chongyang', showing the plant in the field.
Figure 2:
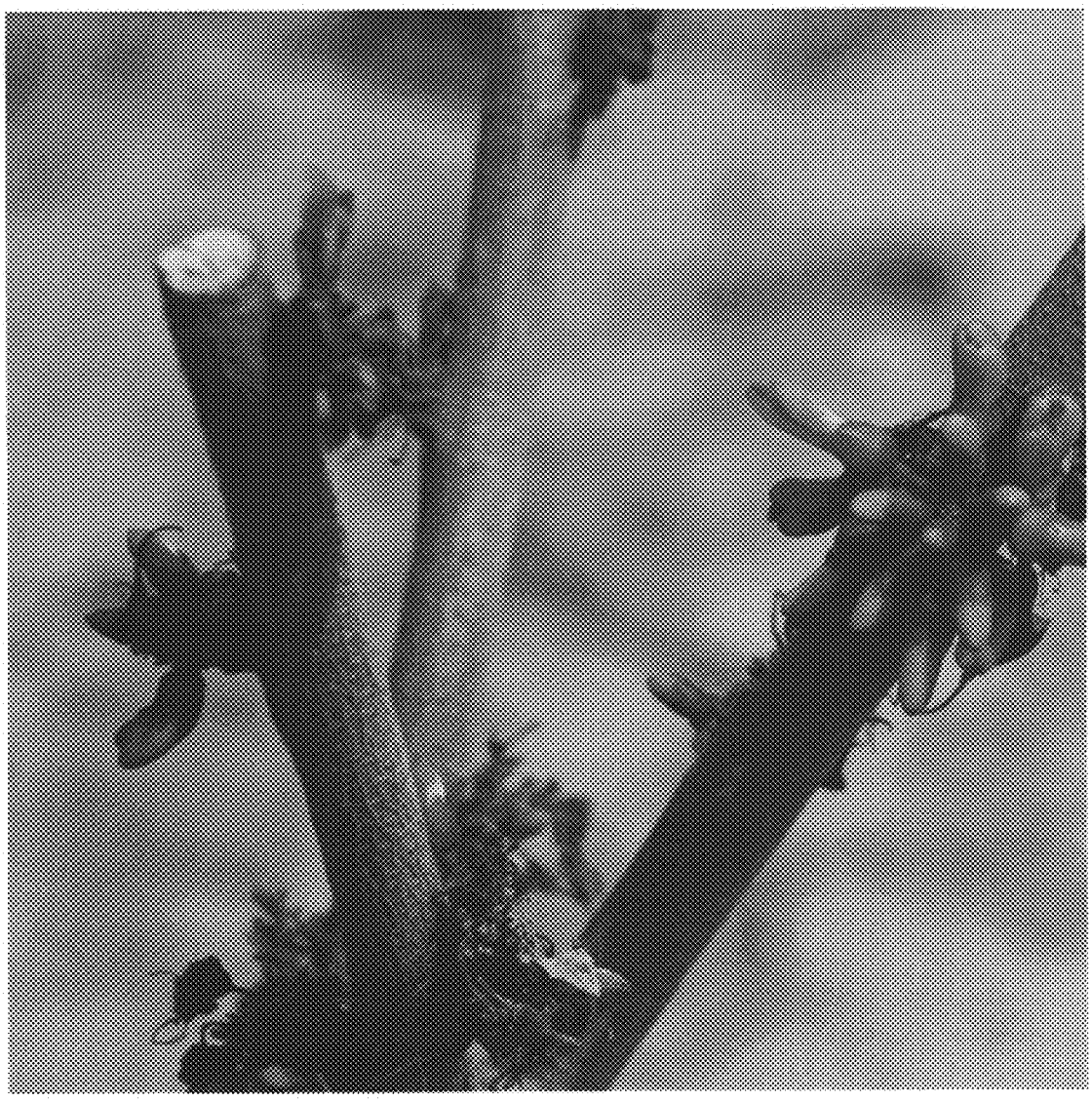
FIG. 2 is a color photograph of the new invention, 'Chongyang', showing its stem.
Figure 3:
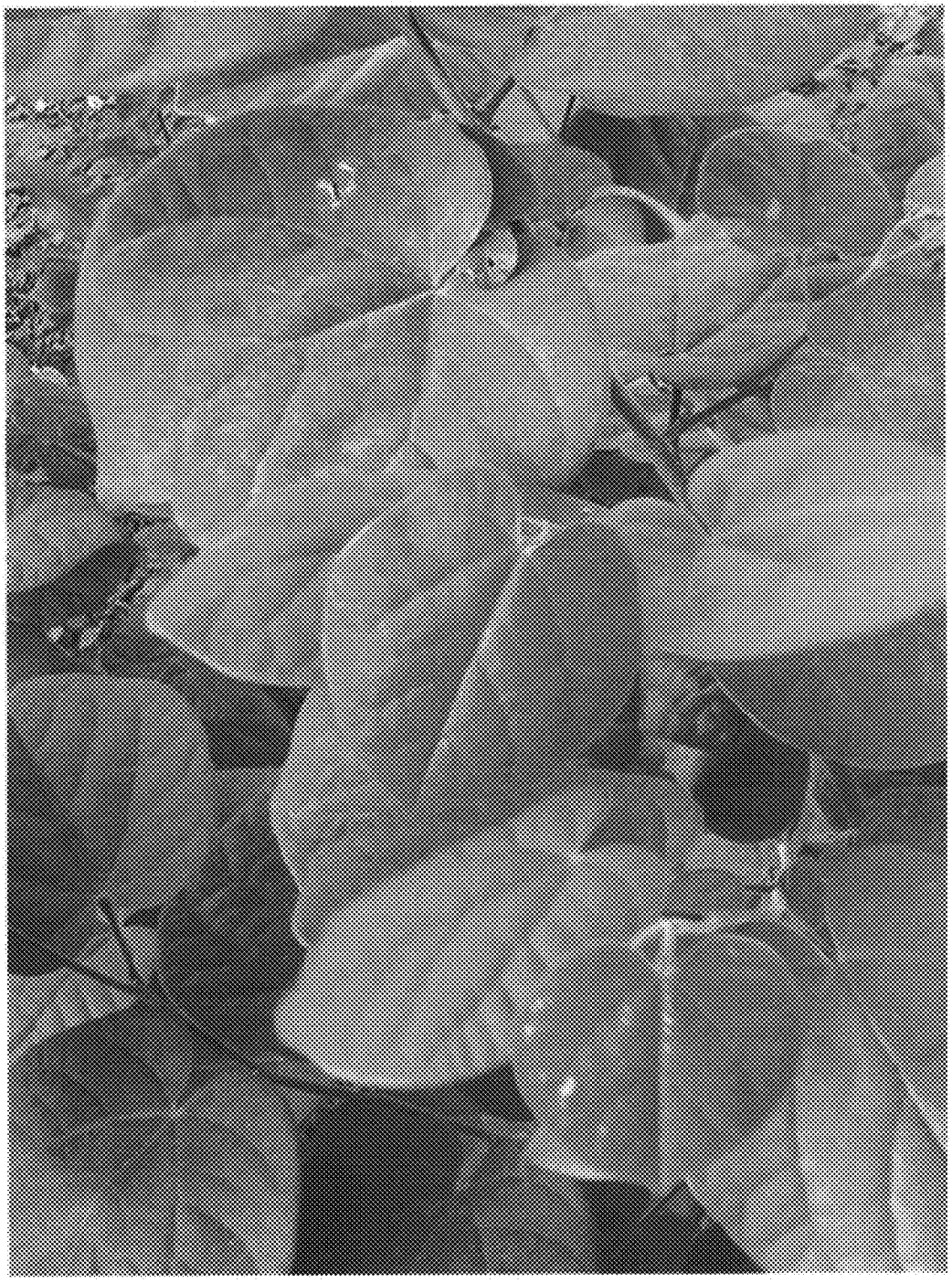
FIG. 3 is a color photograph of the new invention, 'Chongyang', showing its leaves.
Figure 4:
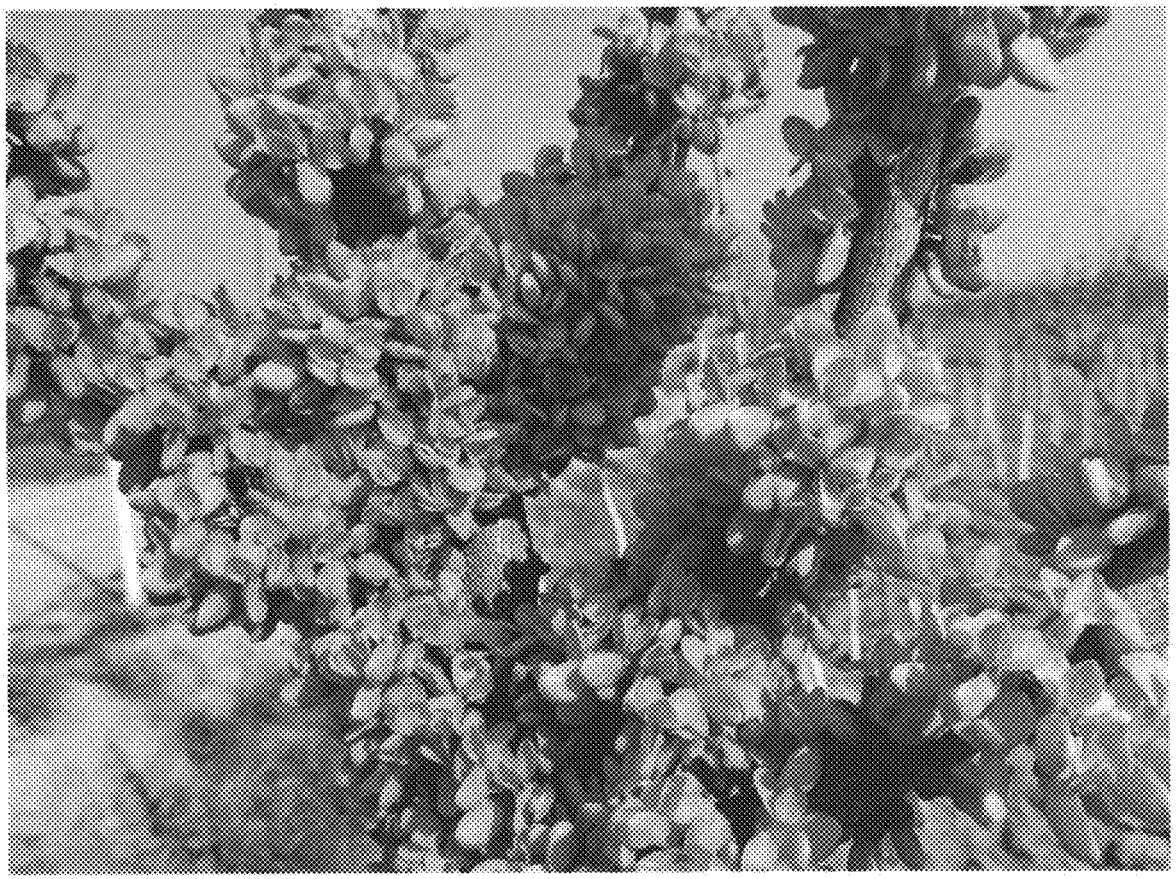
FIG. 4 is a color photograph of the new invention, 'Chongyang', showing the appearance of its flowers in spring.
Figure 5:
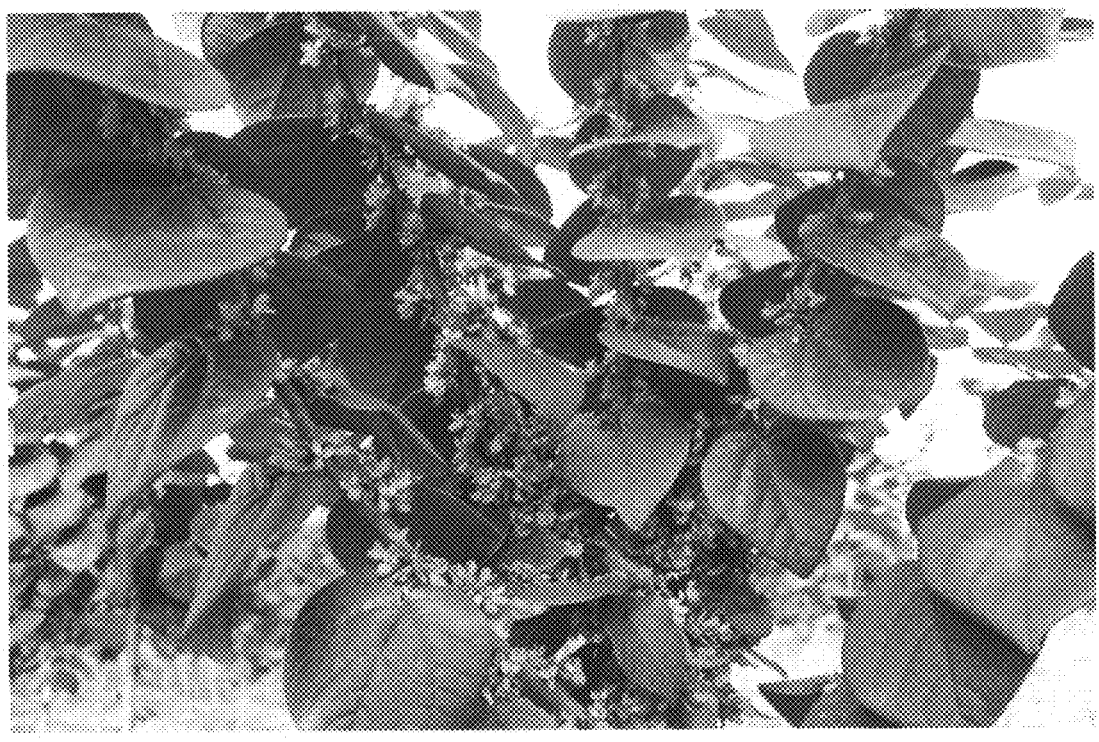
FIG. 5 is a color photograph of the invention, 'Chongyang', showing the appearance of its flowers in autumn.
Figure 6:
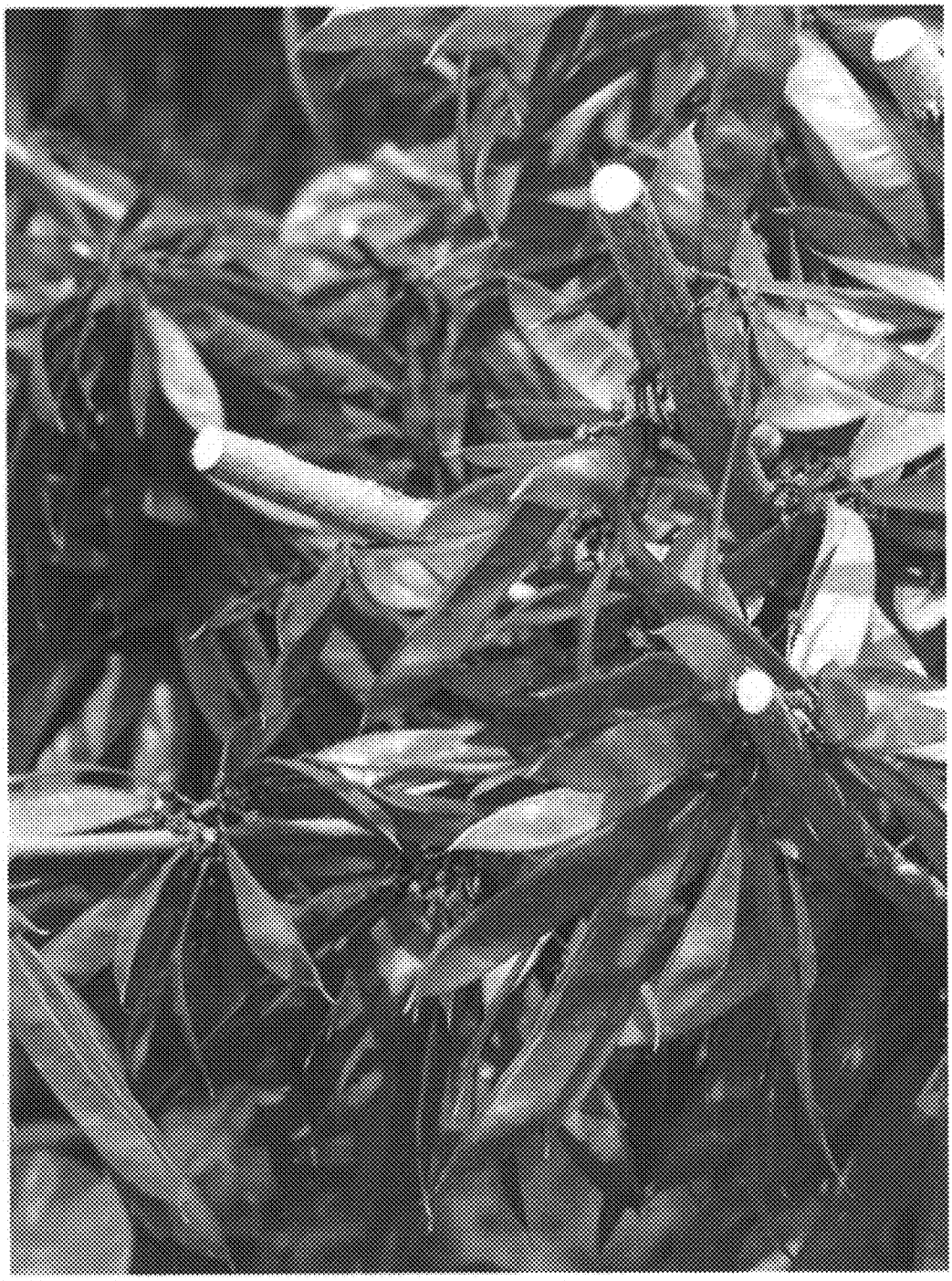
FIG. 6 is a color photograph of the invention, 'Chongyang', showing the appearance of its fruits in spring.
Figure 7:
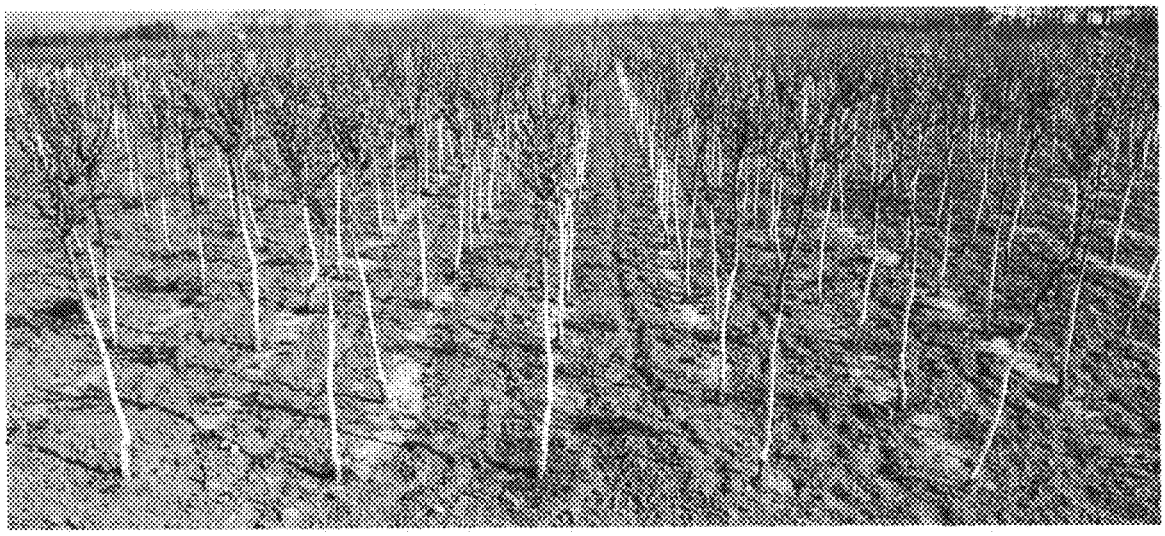
FIG. 7 is a color photograph of the new invention, 'Chongyang', showing the plant in the field in spring.
Figure 8:
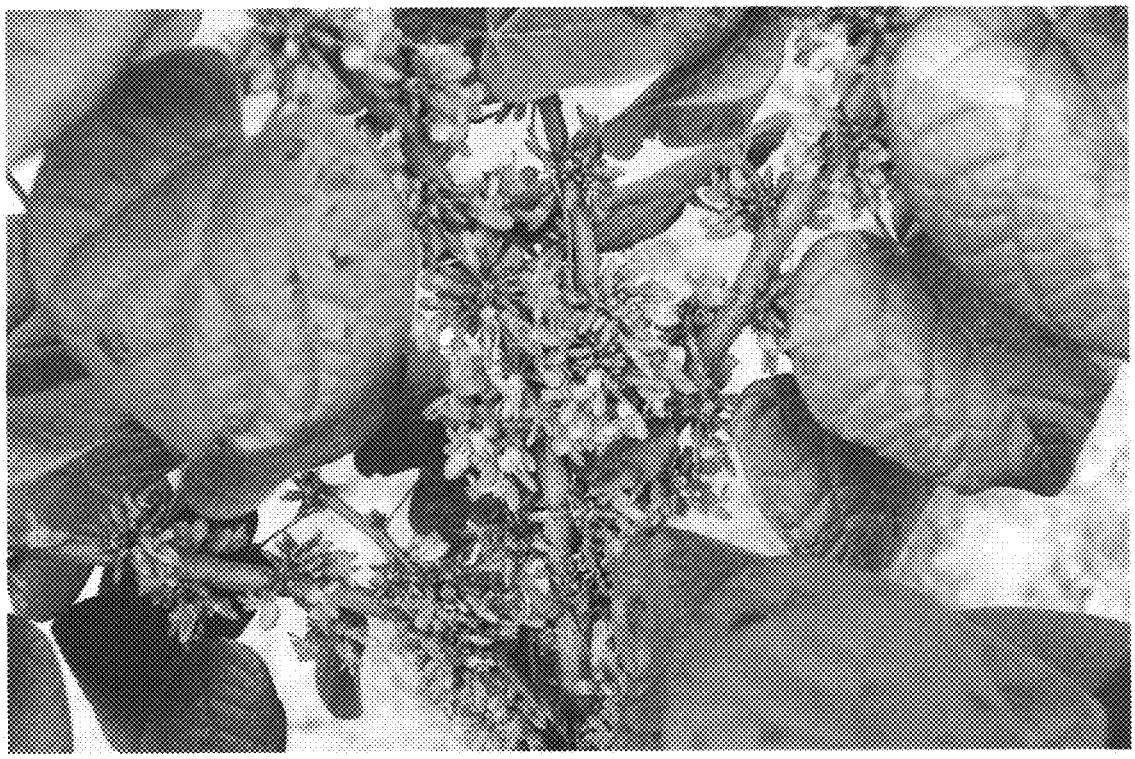
FIG. 8 is a color photograph of the new invention, 'Chongyang', showing the plant in the field in autumn.
Figure 9:
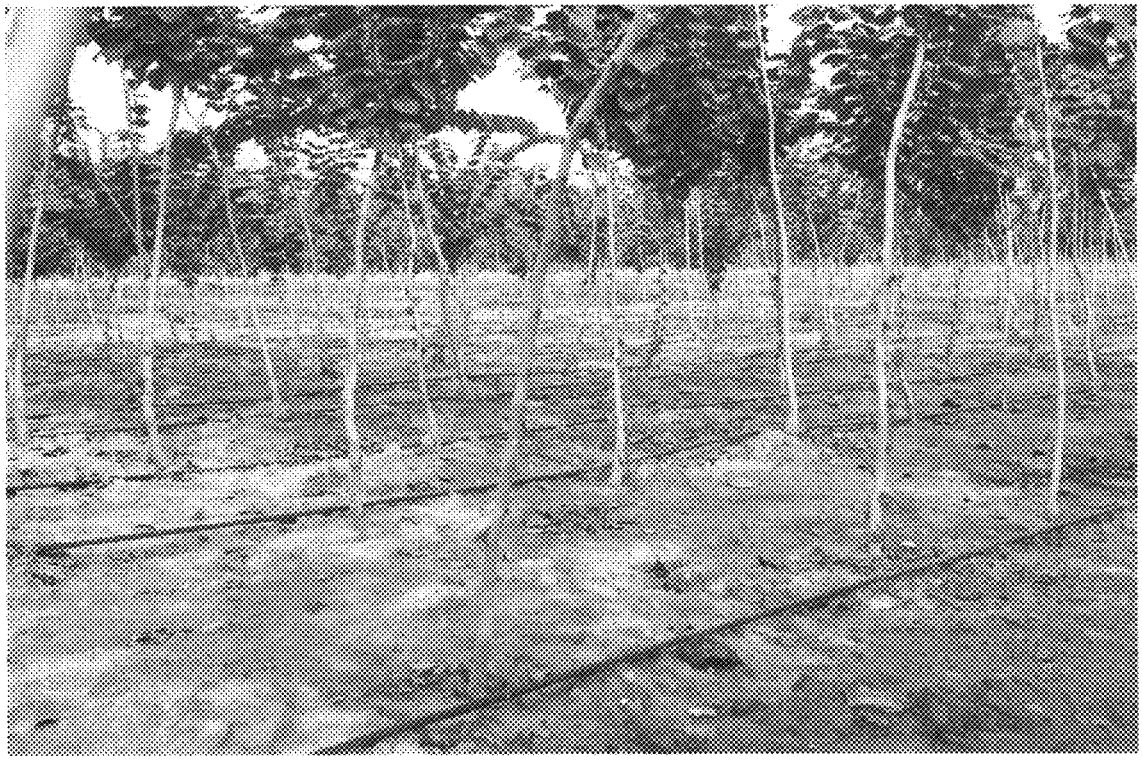
FIG. 9 is a color photograph of the new invention, 'Chongyang', showing its seedling in the field.

'Chongyang' is a distinct variety of Chinese redbud plant, belonging to deciduous-leaved shrubs and small trees. A whole plant is 2-4 m high and planted at about 150 meters above sea level. Twigs are coated or glabrous. Leaves are heart-shaped and green (RHS GREEN 140B to 140A or 143C to 143A), which are smooth and glabrous on top surfaces, and slightly rough and glabrous or slightly coated on bottom surfaces. The leaves are 5-8 cm long and 5-6 cm wide. Flowers are densely clustered, butterfly-shaped and rose-red (RHS RED-PURPLE N57D to N57B or 58D to 58A) with short pedicels. The petioles are 1.8 cm-4.2 cm long. There are two florescences in a year. Referring to FIGS. 2, 4 and 7, a first florescence is from March to April in spring, wherein flowers appear before leaves. Referring to FIGS. 1, 5 and 8, a second florescence is from September to November in autumn, wherein the leaves and the flowers exist at the same time. In autumn, a few flowers bloom out in advance, and then all flowers gradually bloom out. Autumn flowers have a same color as spring flowers, and also have a huge amount. However, the autumn florescence is longer than the spring florescence. The autumn flowers wither after frost. Buds are 0.4 cm-0.6 cm long and 0.2 cm-0.3 cm wide, which are rose red (RHS RED-PURPLE 58A). Inflorescence is clustered. Petals are purplish red (RHS RED-PURPLE N57D to N57B or 58D to 58 A). Sepals are rose red (RHS RED-PURPLE 58B). Peduncles are 0.5 cm-1 cm long. There are one pistil and nine stamens for each flower. Fruits are flat pods which is green (RHS GREEN 141D-A or YELLOW-GREEN N144D-A), wherein a length thereof is 3-8 cm and a width is 1-2.5 cm. A few fruits are produced in spring while no fruit is produced in autumn. Trunks have irregular and longitudinal cracks, and are dark gray (RHS GREY GROUP 201D to 201A). Stems are also dark gray (RHS GREY GROUP 201D to A).

Figure 10:
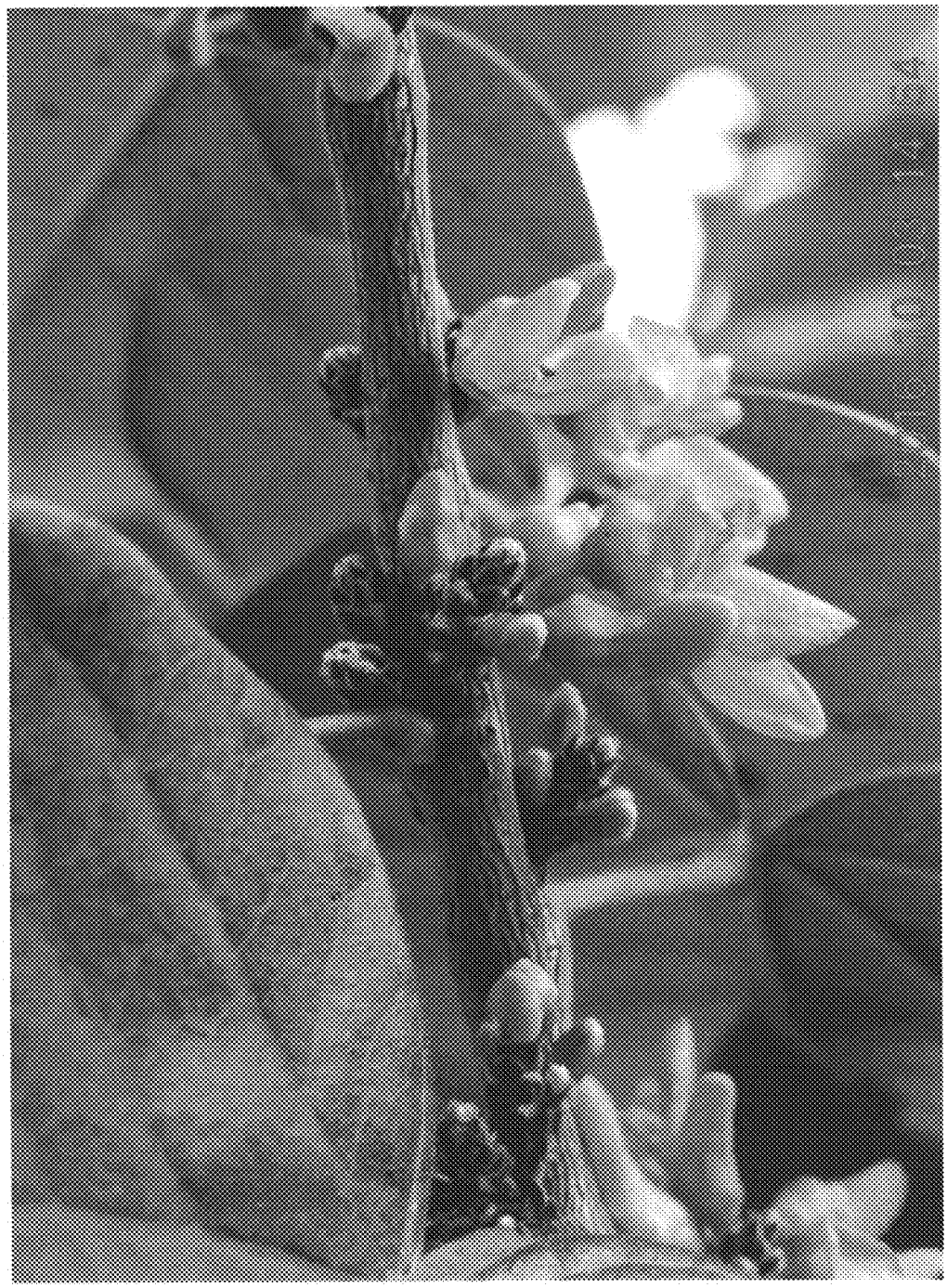
FIG. 10 is a color photograph of the new invention, 'Chongyang', showing the bark of a new-born branch in the field.
Figure 11:
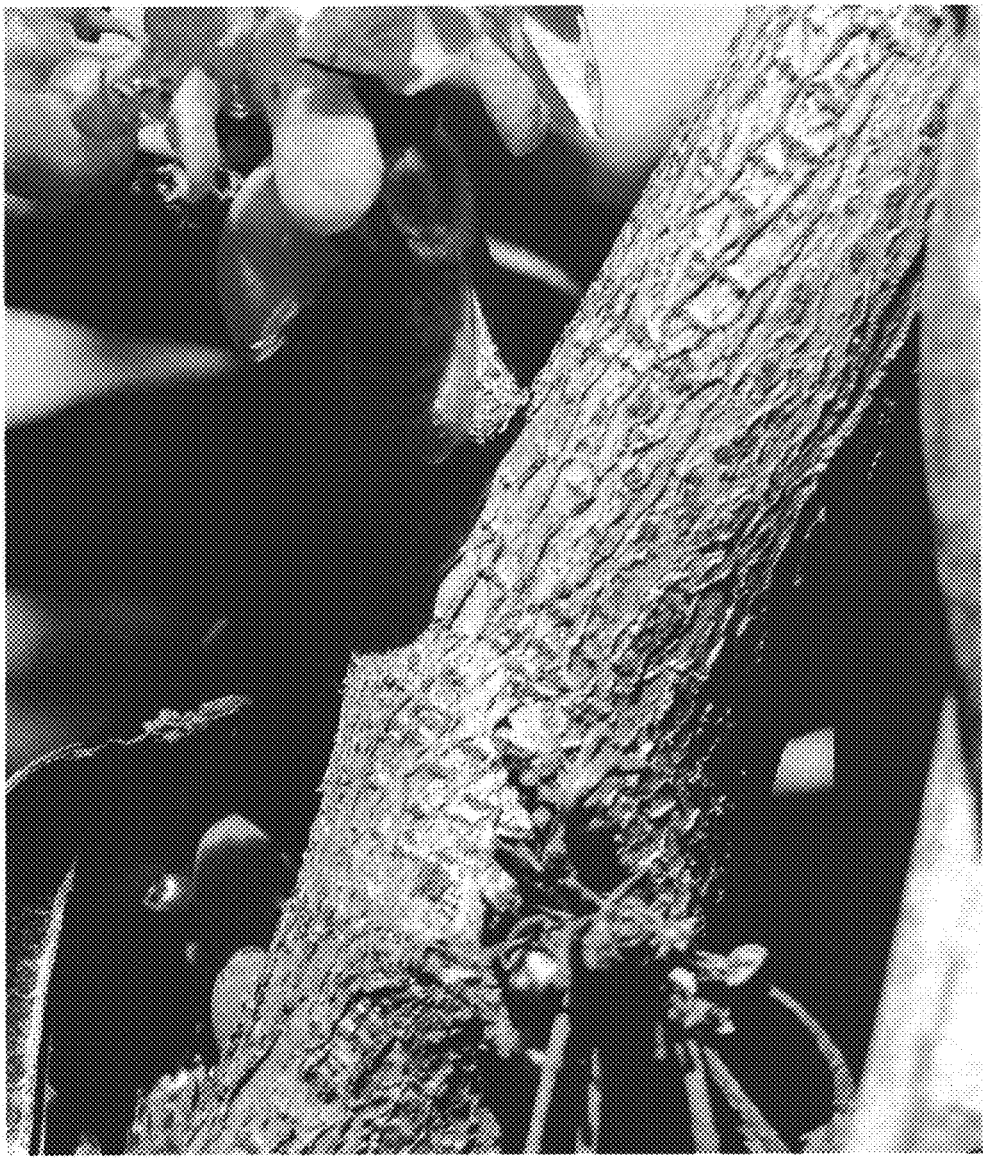
FIG. 11 is a color photograph of the new invention, 'Chongyang', showing the bark of a mature branch in the field.
Figure 12:
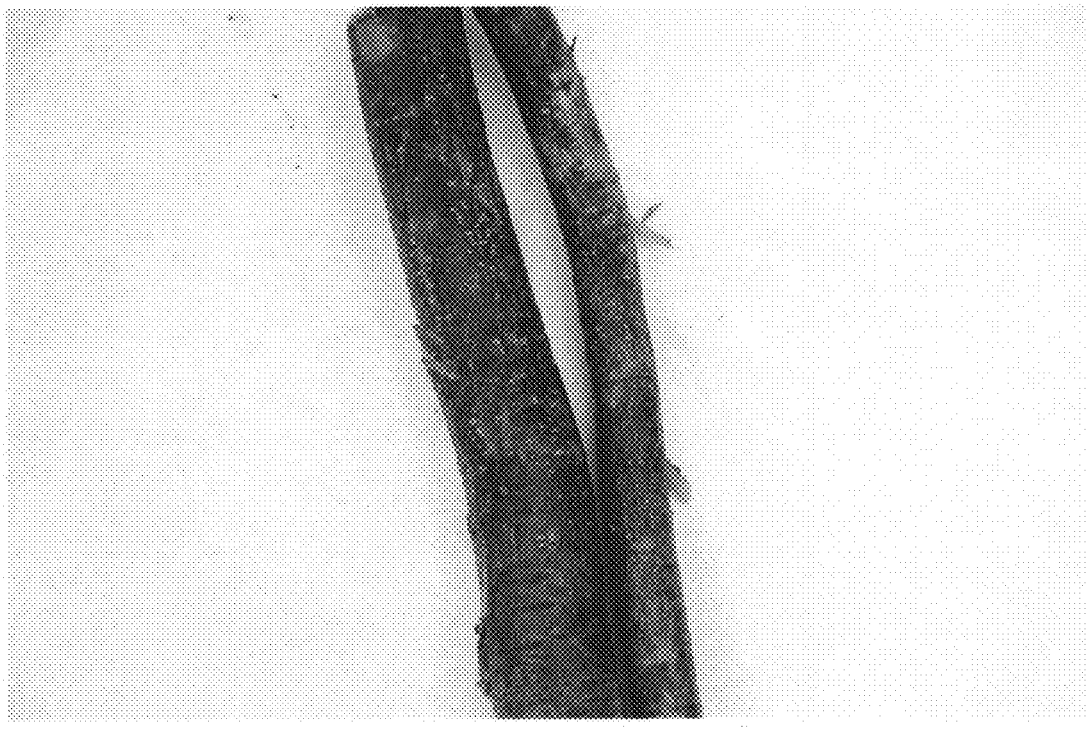
FIG. 12 is a color photograph of the new invention, 'Chongyang', showing the root of the plant in the field.

Referring to FIG. 10, bark of a new-born branch is reddish-brown (RHS GREYED-ORNAGE 175D to 175A) and has vertical cracks. Referring to FIG. 11, bark of perennial mature branch is grayish white (RHS GREYED-WHITE 156D to 156A) and has also vertical crack. Referring to FIG. 12, roots of 'Chongyang' are well developed, which are brown (RHS GREY-BROWN N199D to N199A or BROWN N200A or BLACK 202A).

Figure 13:
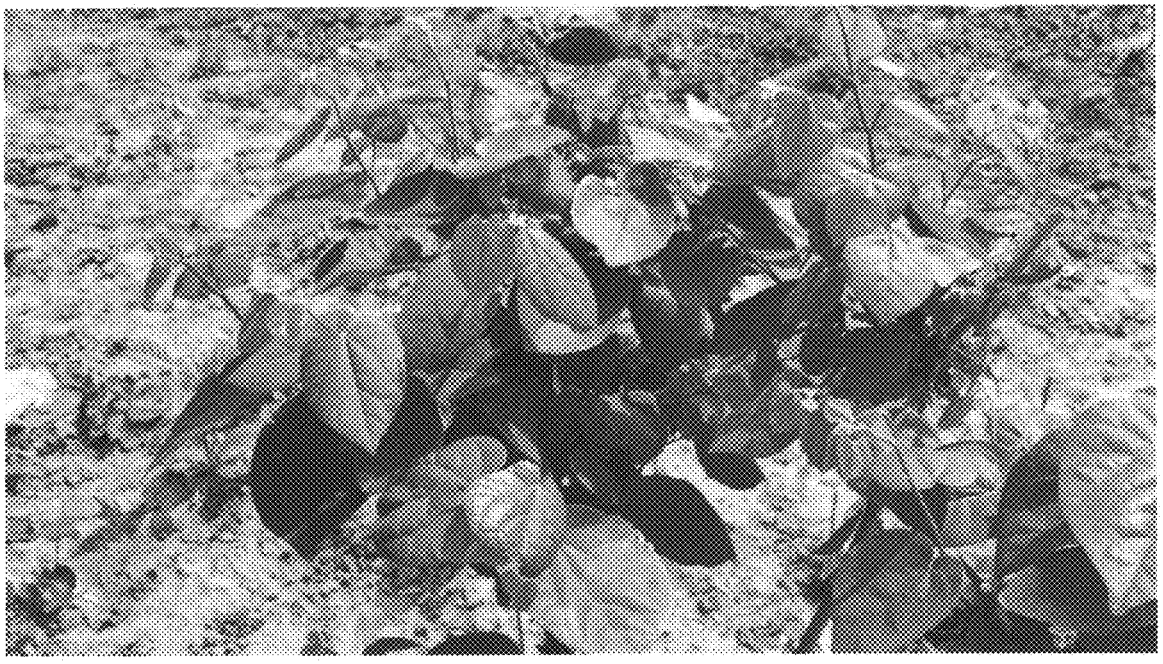
Fig. 13 (prior art)
FIG. 13 is a color photograph of a normal Chinese redbud plant, showing its leaves.
Figure 14:
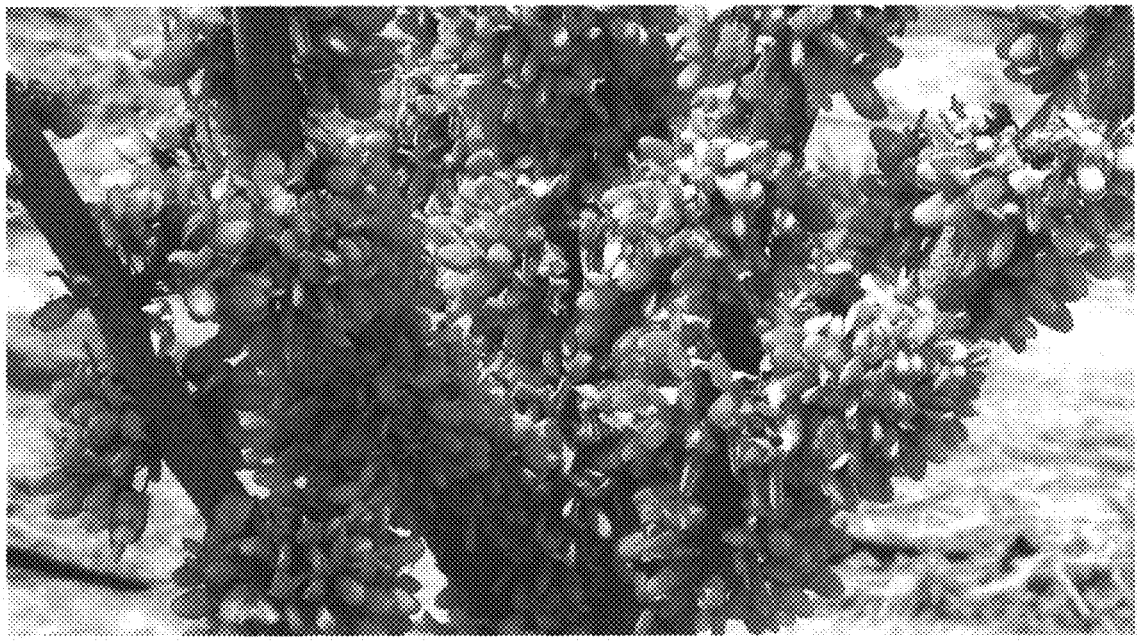
Fig. 14 (prior art)
FIG. 14 is a color photograph of a normal Chinese redbud plant, showing its flowers.

The comparison variety is *Cercis chinensis* Bunge form. *chinensis*, belonging to deciduous-leaved shrubs and small trees. Leaves are heart-shaped and green (RHS GREEN 140B to 140A or 143C to 143A), and are 5-8 cm long and 5-6 cm wide as shown in FIG. 13. Flowers are butterfly-shaped and rose-red (RHS RED-PURPLE N57D to N57B or 58D to 58A) as shown in FIG. 14. There is only one florescence in March to April of a year. wherein flowers appear before leaves. There is no flower autumn, and the leaves fall in early December.

'Chongyang' is a distinctive variety of Chinese redbud plant, which is able to grow in Hubei, Liaoning, Hebei, Shaanxi, Henan, Gansu, Yunnan, Sichuan and other provinces of China. 'Choneyang' is a phototropism species, which has a resistance to minus 23° C. 'Chongyang' grows well with fertile and well-drained soil, and is impatient to water logging. The plant also has resistance to sulfur dioxide, hydrogen fluoride and nitrogen, which is suitable for inhaling harmful gases and decorating.

'Chongyang' is able to be reproduced by grafting, rameting and laying. Grafting is mainly used, with Chinese redbud plant as a rootstock. Seeds are collected from September to October, and are buried in dry sand covered with shade for wintering. The seeds are sowed in coming late March to early April after germination with warm water. Whip grafting should be used from April to May while budding should be used from July to September, wherein external branches facing sunshine are preferred for grafting. During dormancy, the branches for grafting should be stored in refrigerator before germination. During growth, the branches should be picked just before grafting. 7 days after budding or 2 weeks after whip, survival rate should be checked and replantation should be prepared if the survival rate is low. Buds of successfully grated plant should be wiped for ensuring nutrients of the grafted branched.

Specifically, branch-graft in spring has a highest survival rate. Every year, in March or before 'Chongyang' is budded, branches born that year are selected. The branches are cut into about 5 cm long, and bottoms are chamfered, which contains 2-3 buds. Next, the rootstock is cut off flatly, and then vertically cut near one side. The graft material is aligned with one side of the rootstock layer, clamped, and wrapped with a graft plastic film, wherein the buds are left outside. After new leaves are grown, green branches of unmutated species are removed from the rootstocks, so as to the branches of 'Chongyang' grow rapidly. After the plant grows to 2 meters high, it is planted at a row spacing of 3 meters by 4 meters. After 3-4 years, trunks of 'Chongyang' can grow to a diameter of 8 cm at about 150 meters above sea level and can be used in greening of parks or scenic spots.

'Chongyang' should be cultivated in a high and dry place. There is no strict requirement for soil, but sandy soil which is loose and fertile is preferred. Low-lying areas, which are like to suffer water logging, are not suitable for 'Chongyang'. Preferably, seedlings transplant should be done in early April.

'Chongyang' rarely suffers from diseases. Harmful pests are mainly aphids and longhorned beetles. The former can be eliminated by 1500-2000 times imidacloprid spray, and the latter can be eliminated by green Weilei spray or blocking pest holes with drug.

TABLE comparison between 'Chongyang' and normal Chinese redbud.

| | feature | | |
|---|---|---|---|
| name | | Flower feature | Florescence |
| Chongyang | Spring flowers | flowers appear before leaves | March to April |
| | Autumn flowers | leaves and the flowers exist at the same time | September to November |
| Chinese redbud | Spring flowers | flowers appear before leaves | March to April |

These features and other characteristics of the plant are apparent from the figures.

What is claimed is:

1. A new and distinct variety of Chinese redbud plant named 'Chongyang', substantially as described and illustrated.

* * * * *